US00PP30791P3

(12) United States Plant Patent
Meier

(10) Patent No.: US PP30,791 P3
(45) Date of Patent: Aug. 13, 2019

(54) ***GAULTHERIA* PLANT NAMED 'GAULBRI 1'**

(50) Latin Name: *Gaultheria procumbens*
Varietal Denomination: Gaulbri 1

(71) Applicant: Gurjit Sidhu, Mission (CA)

(72) Inventor: Corey Meier, Centralia, WA (US)

(73) Assignee: Gurjit Sidhu, Mission, BC (CA)

( * ) Notice: Subject to any disclaimer, the term of this patent is extended or adjusted under 35 U.S.C. 154(b) by 0 days.

(21) Appl. No.: 15/932,415

(22) Filed: Feb. 27, 2018

(65) Prior Publication Data

US 2018/0352708 P1 Dec. 6, 2018

(30) Foreign Application Priority Data

Jun. 5, 2017 (CA) ..... PBR 17-9240

(51) Int. Cl.
*A01H 5/00* (2018.01)
*A01H 6/00* (2018.01)
*A01H 5/08* (2018.01)

(52) U.S. Cl.
USPC ..... Plt./226
CPC ..... *A01H 6/00* (2018.05); *A01H 5/08* (2013.01)

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Gaultheria procumbens* plant named 'Gaulbri1' that is characterized by its foliage that is variegated with green centers and margins that are white to pink in color with some sectional variegation that is white, light green, pink and dark green in color, and its berries that are pink in color when young and turn red in color when they mature.

2 Drawing Sheets

Botanical classification: *Gaultheria procumbens.*
Cultivar designation: 'Gaulbri1'.

BACKGROUND OF THE INVENTION

The present invention relates to a new and distinct cultivar of *Gaultheria procumbens*, known as *Gaultheria* 'Gaulbri1' and is hereinafter referred to by its cultivar name 'Gaulbri1'.

'Gaulbri1' was found as a natually-occuring variegated branch mutation of an unnamed and unpatented plant of *Gaultheria procumbens* by the Inventor that was growing in a container in a production block at a nusery in Elma, Wash. in spring of 2015.

Asexual propagation of the new cultivar was first accomplished by tissue culture using meristemac tissue under the direction of the Inventor in Elma, Wash. in July of 2015. Asexual propagation of the new cultivar by tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Gaulbri1' as a new and unique cultivar of *Gaultheria.*

1. 'Gaulbri1' exhibits foliage that is variegated with green centers and margins that are white to pink in color with some sectional variegation that is white, light green, pink and dark green in color.
2. 'Gaulbri1' exhibits berries that are pink in color when young and turn red in color when they mature.

The parent plant of 'Gaulbri1' is similar to 'Gaulbri1' in flower and berry color, but differs from 'Gaulbri1' in having leaves that are solid dark green in color. 'Gaulbri1' can be most closely compared to *Gaultheria procumbens* cultivars 'Gaulsidh11' (U.S. Plant patent application Ser. No. 29,094)* and 'Gaulsidh5' (U.S. Plant Pat. No. 29,093)*. Both are similar to 'Gaulbri1' in plant habit and in having flowers that are white in color and mature berries that are red in color. 'Gaulsidh11' differs from 'Gaulbri1' in having leaves that are solid dark green in color and a higher berry set. 'Gaulsidh5' differs from 'Gaulbri1' in having larger berries and leaves that are solid green in color.

* Examiner has permission to replace the U.S. Plant Patent Application Nos. with U.S Plant Patent Nos. and delete this statement.

BRIEF DESCRIPTION OF THE DRAWINGS

The accompanying colored photographs illustrate the overall appearance and distinct characteristics of the new *Gaultheria*. The photographs were taken of a plant 2 years in age as grown in a poly greenhouse in Elma, Wash.

The photograph in FIG. 1 provides a side view of 'Gaulbri1' in fruit.

Figure 1:
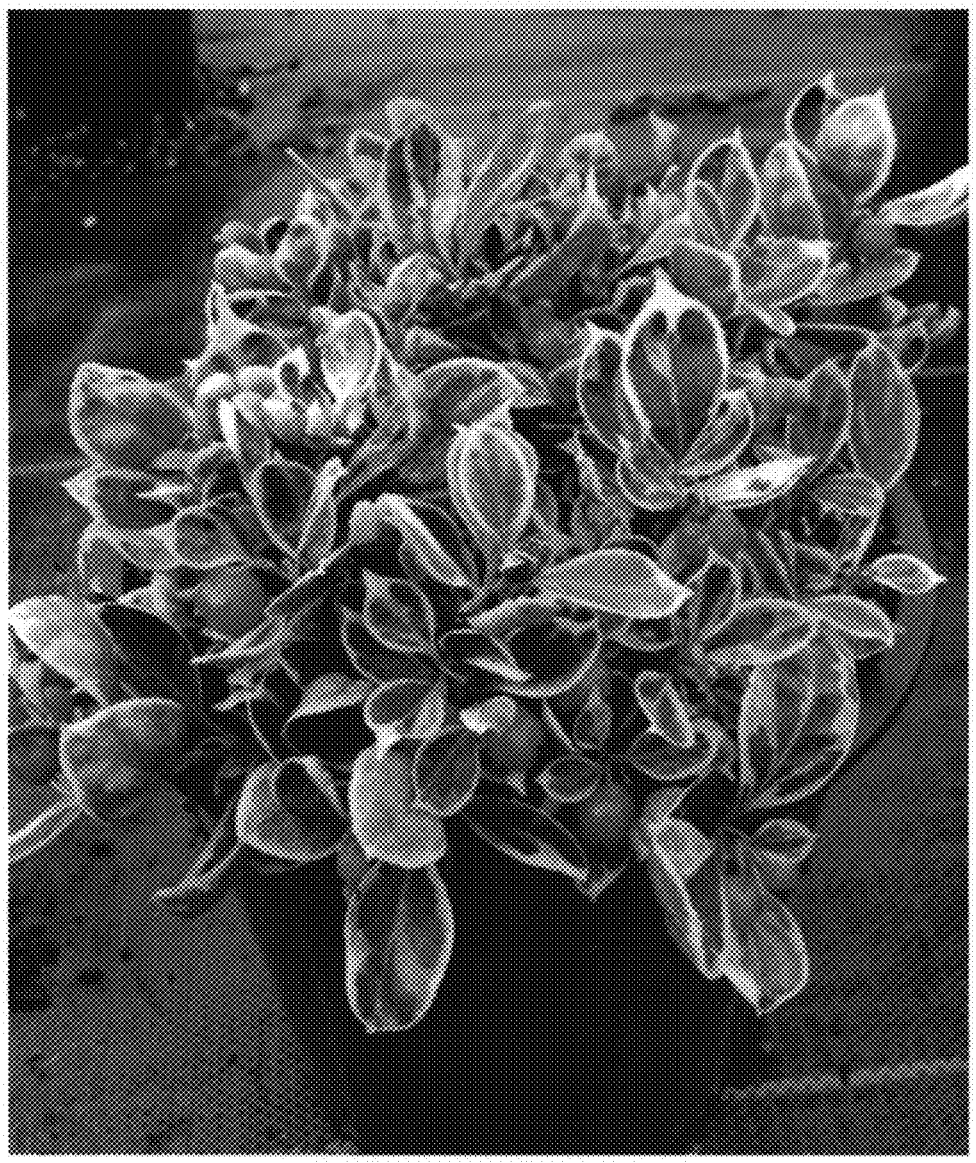
Figure 2:
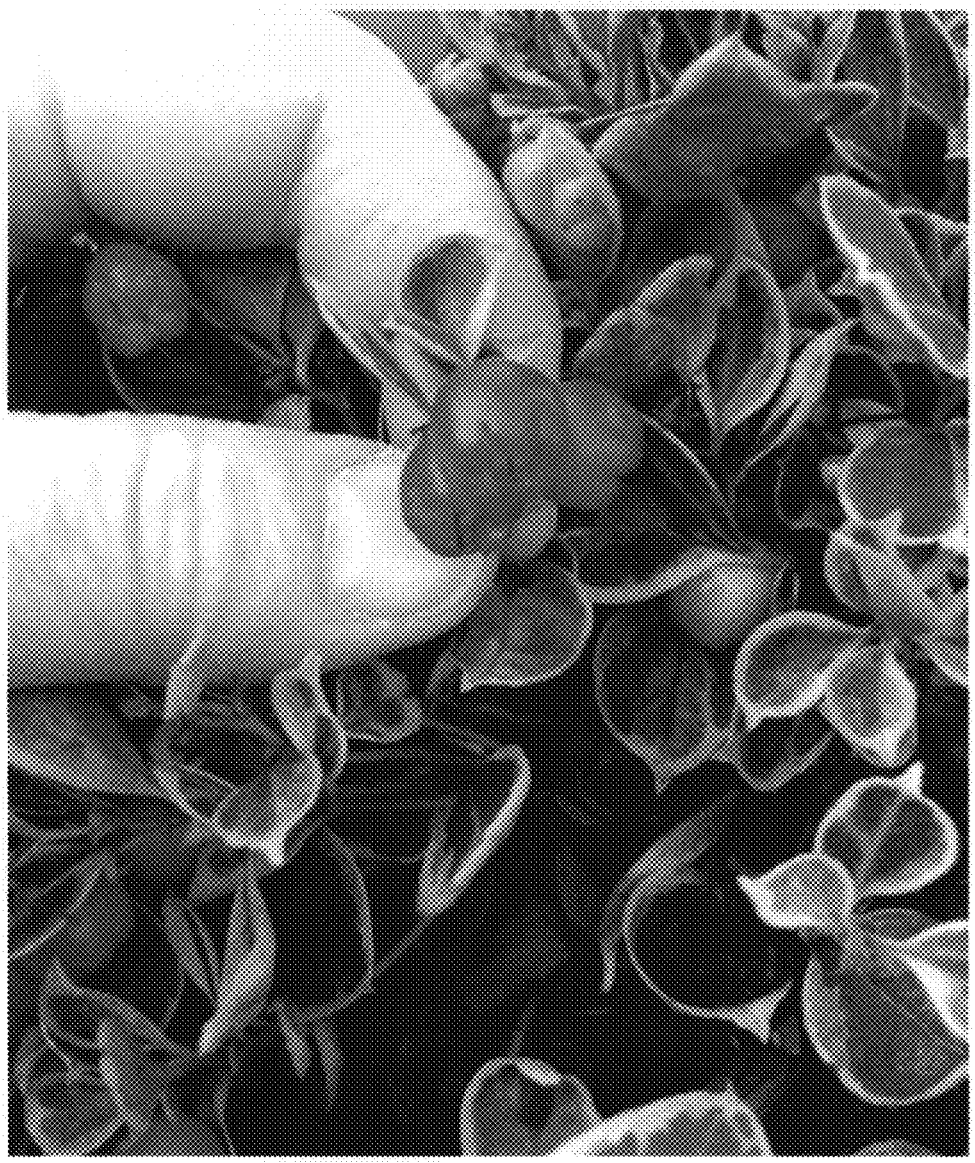

The photograph in FIG. 2 provides a close-up view of the fruit and foliage of 'Gaulbri1'.

The colors in the photographs may differ slightly from the color values cited in the detailed botanical description, which accurately describe the colors of the new *Gaultheria.*

DETAILED BOTANICAL DESCRIPTION OF THE PLANT

The following is a detailed description of 2.5-year-old plants of the new cultivar grown outdoors in 1-gallon containers in St. Thomas, Ontario, Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Four to six weeks from late spring to late summer in Ontario, Canada.

*Plant type*.—Evergreen shrub.

*Plant habit*.—Broadly spreading groundcover once established.

*Height and spread*.—An average of 15 cm in height and 30 cm in width.

*Hardiness*.—At least in U.S.D.A. Zones 3 to 8.

*Diseases and pests*.—No resistance or susceptibility to diseases or pests has been observed.

*Propagation*.—Tissue culture.

*Root development*.—2 to 3 weeks to initiate roots in tissue culture, an average of 12 months to fully root in a liner.

*Growth rate and vigor*.—Moderate.

Stem description:

*Shape*.—Round.

*Stem color*.—New stem; 60A, mature; 146D suffused with 185C to 185D.

*Stem size*.—An average of 8.7 cm in length and 1 mm in width.

*Stem surface*.—Young stems moderately glossy.

*Stem strength*.—Medium.

*Branching*.—Freely branched, an average of 14 basal branches.

*Branch angle*.—Upright to outward.

*Branch internode length*.—Up to 4 mm.

Foliage description:

*Leaf shape*.—Elliptic to obovate.

*Leaf division*.—Simple.

*Leaf base*.—Cuneate.

*Leaf apex*.—Cuspidate.

*Leaf fragrance*.—Wintergreen if crushed.

*Leaf venation*.—Pinnate, young leaf color; mid vein of upper surface 144A, mid vein of lower surface 145A, mature leaf color; mid vein of upper surface 196A and 62C towards base, mid vein of lower surface; 148B and 51B towards base.

*Leaf margins*.—Irregularly serrate, single small hair emerging from the tip of each tooth, up to 1 mm in length and 166A in color.

*Leaf arrangement*.—Alternate and clustered near tips.

*Leaf attachment*.—Petiolate.

*Leaf number*.—Average of 9 per branch.

*Leaf surface*.—Upper and lower surface; glabrous, dull and leathery.

*Leaf variegation*.—Present.

*Leaf size*.—Average of 3.7 cm in length and 2.2 cm in width.

*Leaf color*.—Emerging leaves upper surface; ranging from 174A to 166B to 164A, margins 62A to 62B, emerging leaves lower surface, 176B, margins 62C, young leaves upper surface; 144A, flushed with 137A with some sections of 191B, young leaves lower surface; N155B suffused with 62C to 62D, mature leaves upper surface; 138A with random sections of N189C, margins 158A, mature leaves lower surface; 148B, margins 158A, fall foliage; upper surface; 200A with sections of 195A, margins between 51B and 155A, lower surface; between 197A and 194A, suffused with 51C, margins between 51B and 155A.

*Petioles*.—Average of 4.8 mm in length and 1.8 mm in width, upper and lower surfaces are dull, color of upper and lower surfaces; a blend of 51C and 181C.

Inflorescence description:

*Inflorescence*.—Axillary and terminal clusters of individual flowers.

*Inflorescence size*.—Average of 4.7 cm in length.

*Lastingness of inflorescence*.—Average of 2 weeks, self cleaning (sepals and petals).

*Number of flowers*.—4 to 10 per flowering branch, average of 150 per plant.

*Flower buds*.—Ovate in shape, average of 4 mm in length and 3 mm in width, color NN155B suffused with 63C towards base, satiny surface.

*Flower size*.—Average of 7 mm in length and 6 mm in width.

*Corolla*.—Urceolate in shape, comprised of 5 fused ovate shaped petals with rounded tips (5%) free that are moderately reflexed, free parts are 1.5 mm in length and 1 mm width, width of aperature 4 mm, color NN155B on both surfaces, when opening and mature, both surfaces are satiny and glabrous and very slightly ribbed on inner and outer surfaces.

*Calyx*.—Rotate in arrangement, average of 2 mm in depth and 6 mm in diameter.

*Sepals*.—5, ovate in shape with base fused (lower 25% fused into ring), average of about 1.5 mm in length and width, acute apex, color 155B suffused with 62B towards base, satiny on both surfaces.

*Bracts*.—2 small bracts, an average of 1 mm in length and width, ovate in shape, truncate base, acute apex, glossy on both surfaces, color 155B suffused with 62B.

*Peduncles*.—Round, curved to hang downward, an average of 7 mm in length and 1 mm in width, color 155C suffused with 62B and 54C, pubescent surface.

*Pedicels*.—None, peduncles arise directly from stem node.

Reproductive organs:

*Androecium*.—Stamens; average of 10, anthers; dorsifixed, narrow deltoid in shape, 60B in color and 2 mm in length, filaments; oblong in shape, 4 mm in length, 1 mm in width and 155B in color, highly pubescent, pollen; moderate in quantity and NN155C in color.

*Gynoecium*.—Pistil; 1, stigma; club-shaped, 1 mm in length and width, 145D in color, style; average of 6 mm in length, 157D in color, ovary; round in shape, 6-parted, 2.5 mm in diameter and depth, 145C in color.

Fruit description:

*Type*.—Berry.

*Number*.—Average of 3 per lateral branch.

*Fruit size*.—Up to 9 mm in length and 10 mm in width.

*Fruit skin color*.—Young fruit; 47D, mature fruit; 45B.

*Fruit flesh*.—155B in color, glistening and spongy in texture.

*Fruit surface*.—Glossy and glabrous.

*Fruit shape*.—Oblate with indented apex and 5 bluntly acute extended tips, tip size is 3 mm in length and 5 mm in width.

*Mature ovary*.—Oblate in shape, dull and papery in texture, average of 2.9 mm in length and 4.2 mm in width, persistent style, 3 mm in length.

*Seeds*.—Approximately 28 cylindrical shaped seeds, glossy surface, less than 1 mm in length and width, 160D in color.

It is claimed:

1. A new and distinct cultivar of *Gaultheria* plant named 'Gaulbri1' as herein illustrated and described.

* * * * *